Aug. 25, 1964 E. S. BOERNER Plant Pat. 2,441
ROSE PLANT
Filed Oct. 16, 1963
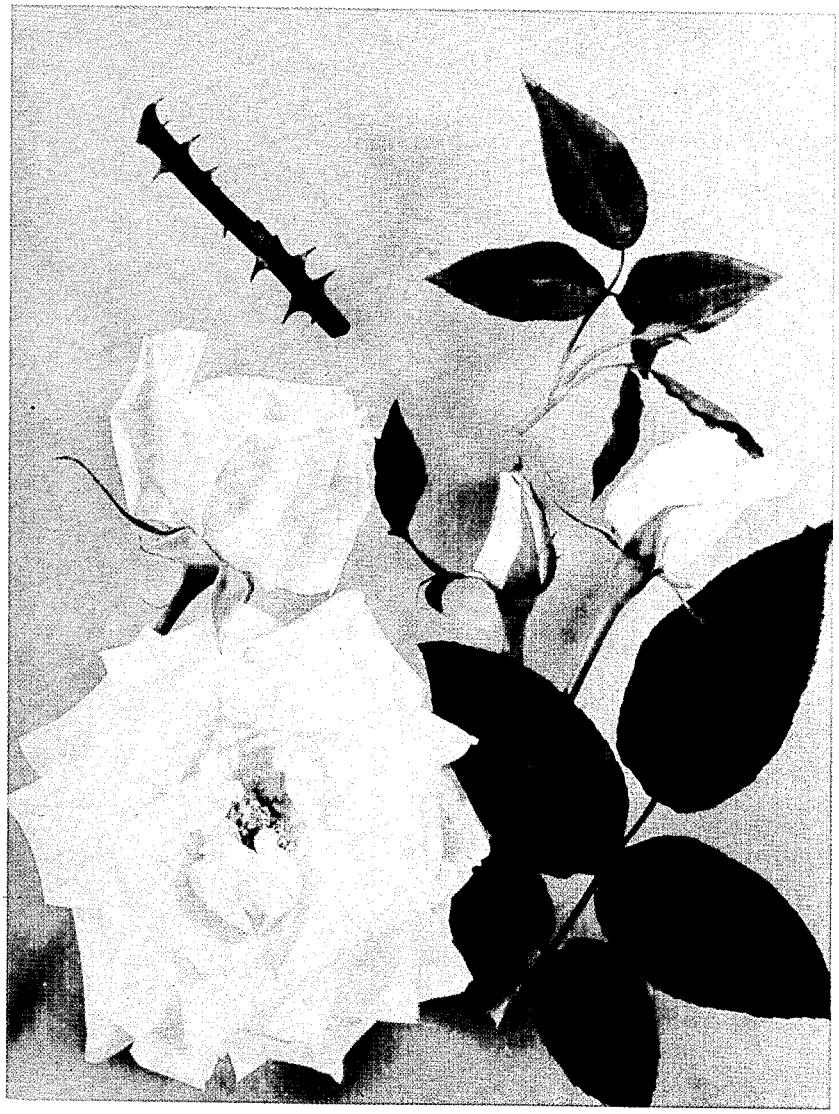
Inventor
E. S. Boerner
By: Robb & Robb
Attorneys.

United States Patent Office

Plant Pat. 2,441
Patented Aug. 25, 1964

2,441
ROSE PLANT

Eugene S. Boerner, Newark, N.Y., assignor to Jackson & Perkins Company, Newark, N.Y., a corporation of New York Filed Oct. 16, 1963, Ser. No. 316,787
1 Claim. (Cl. Plt.—14)

The present invention relates to a new and distinct variety of rose plant of the hybrid tea class, which was originated by me by crossing an unnamed and unpatented white seedling with the variety known as "White Queen" (Plant Patent No. 1,762).

The primary objective of this breeding was to produce a new and improved rose variety of the hybrid tea class and which bears white flowers of high-centered form. This objective was fully achieved, along with other desirable improvements, as evidenced by the following unique combination of characteristics which are outstanding in the new variety and which distinguish it from its parents, as well as from all other varieties of which I am aware:

(1) A large plant size;
(2) Prolific flower production;
(3) Long flower stems;
(4) Attractive green tinted (green-yellow) buds which retain this color to the half open stage;
(5) A large, high-centered, open flower form;
(6) A distinctive and attractive white flower color in the open flower stage; and
(7) Long lasting qualities of the flowers.

Asexual reproduction of my new variety by budding, as performed at Newark, New York, and also at Pleasanton, California, shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.
*Seed parent.*—An unnamed white seedling.
*Pollen parent.*—"White Queen."

Classification:
*Botanic.*—Hybrid tea.
*Commercial.*—Hybrid tea.

*Flower*

(Observations made from specimens grown in a greenhouse at Newark, New York, in the early morning during the latter part of the month of August.)

Blooming habit: Recurrent—continuous.

Bud:
*Size.*—Large.
*Form.*—Ovoid; is not affected by wet or hot weather.
*Color.*—When sepals first divide—Pale Viridine Yellow, Plate 5. When petals begin to unfurl—Pale Green-Yellow, Plate 5. When half-blown: inside of petals—White, Plate 51; reverse of petals—White, Plate 51, with lower half of petals very lightly overcast with Pale Glass Green, Plate 31.
*Sepals.*—Branched; curl back when petals begin to unfurl. Color: inside—Malachite Green, Plate 32; outside—Light Bice Green, Plate 17.
*Calyx.*—Color—Bice Green, Plate 17. Shape—pear. Size—long. Aspect—smooth. Odor when rubbed—none.

*Peduncle.* — Length — long. Aspect — rough. Strength—erect; heavy. Color—Spinach Green, Plate 5.
*Opening.*—Opens up well; is not affected by adverse weather conditions.

Bloom:
*Size.*—Very large. Average size when fully expanded—from 5 inches to 5½ inches.
*Borne.*—Both singly and several together.
*Stems.*—Long; strong.
*Form (when first open).*—High-centered. Permanence—retains its form to the end.
*Petalage.*—Double (full but open center). Number of petals under normal conditions—45 to 50.
*Color.*—Center of flower—White, Plate 51, very lightly overcast with Sea-Foam Yellow, Plate 31, at base. Outer petals—White, Plate 51. Base of petals (aiglet)—Pale Chalcedony Yellow, Plate 17. Inside of petals—White, Plate 51. Reverse of petals—White, Plate 51. General tonality from a distance—White, Plate 51.
*Discoloration.*—General tonality at end of first day—White, Plate 51. Second day—White, Plate 51. Third day—White, Plate 51.

Petals:
*Texture.*—Leathery; is not affected by wet or hot weather.
*Appearance.*—Inside—satiny. Outside—shiny.
*Form.*—Oval.
*Arrangement.* — Imbricated (regularly arranged shingle-like).
*Petaloids in center.*—Few; large.
*Persistence.*—Drop off cleanly.
*Fragrance.*—Moderate. Nature—tea (average hybrid tea scent).
*Lasting quality.*—On plant—very long. As cut flower—very long.

*Genital Organs*

Stamens, anthers: Medium size; many; regularly arranged around styles. Color—Antimony Yellow, Plate 15.
Stamens, filaments (threads): Medium length. Color—Glass Green, Plate 31.
Pollen: Color—Light Buff, Plate 15.
Styles: Bunched; even length; medium length; thin.
Stigmas: Color—Tilleul-Buff, Plate 40.
Ovaries: All enclosed in calyx.
Hips: None.
Seeds: None.

*Plant*

Form: Bush; large plant size.
Growth: Vigorous; upright.
Foliage: Compound of 5–7 leaflets.
*Size.*—Very large.
*Quantity.*—Normal.
*Color.*—New foliage: upper side—Courge Green, Plate 17, with outer edge Oxblood Red, Plate 1; under side—Van Dyke Red, Plate 13. Old foliage: upper side—Dark Cress Green, Plate 31; under side—Cress Green, Plate 31.
*Shape.*—Oval pointed.
*Texture.* — Upper side — leathery. Under side—smooth.
*Ribs and veins.*—Ordinary.
*Edge.*—Serrated (saw-toothed).
*Serration.*—Both double and single; small.
*Leaf stem.*—Color—Diamine Brown, Plate 13. Under side—prickly.
*Stipules.*—Long; slightly serrated.

Wood:

*New wood.*—Color—Oil Green, Plate 5. Bark—smooth.

*Old wood.*—Color—Yew Green, Plate 31. Bark—smooth.

Thorns:

*Thorns.*—Quantity: on main stalks from base—ordinary; on laterals from stalk—ordinary. Form—flat base; medium length; hooked downward. Color (when young)—Hellebore Red, Plate 38. Position—irregular.

*Prickles.*—Quantity: on main stalks—none; on laterals—none.

*Short needles.*—Quantity: on main stalks—none; on laterals—none.

I claim:

A new and distinct variety of rose plant of the hybrid tea class, substantially as herein shown and described, characterized particularly as to novelty by the unique combination of a large plant size, prolific flower production, long flower stems, green-yellow buds in which the greenish tint persists to the half open bud stage, a large, high-centered, open flower form, a distinctive and attractive white flower color in the open stage, and long lasting qualities of the flowers.

No references cited.